United States Patent
Badia

(10) Patent No.: US 8,651,865 B2
(45) Date of Patent: Feb. 18, 2014

(54) SET OF ONE-PIECE ANGLED ABUTMENTS

(76) Inventor: Vicente Gabriel Faus Badia, Valencia (ES)

( * ) Notice: Subject to any disclaimer, the term of this patent is extended or adjusted under 35 U.S.C. 154(b) by 0 days.

(21) Appl. No.: 12/798,494

(22) Filed: Apr. 5, 2010

(65) Prior Publication Data

US 2010/0266986 A1  Oct. 21, 2010

Related U.S. Application Data

(63) Continuation-in-part of application No. 11/442,654, filed on May 26, 2006, now abandoned.

(30) Foreign Application Priority Data

Oct. 10, 2005 (ES) .................................. 2005022461

(51) Int. Cl.
- *A61C 13/38* (2006.01)
- *A61C 8/00* (2006.01)
- *A61B 19/02* (2006.01)
- *B65D 83/10* (2006.01)

(52) U.S. Cl.
USPC ............. 433/174; 433/77; 206/63.5; 206/368

(58) Field of Classification Search
USPC ........... 433/172–176, 201.1, 202.1, 215, 220, 433/221, 77; 206/63.5, 83, 368–369
See application file for complete search history.

(56) References Cited

U.S. PATENT DOCUMENTS

| | | | | |
|---|---|---|---|---|
| 1,437,596 A | * | 12/1922 | Korb | 206/369 |
| 4,203,518 A | * | 5/1980 | Current | 206/380 |
| 4,531,915 A | * | 7/1985 | Tatum, Jr. | 433/173 |
| 4,988,297 A | * | 1/1991 | Lazzara et al. | 433/173 |
| 5,030,095 A | | 7/1991 | Niznick | |
| 5,052,929 A | | 10/1991 | Seal | |
| 5,092,771 A | * | 3/1992 | Tatum, III | 433/173 |
| 5,135,395 A | * | 8/1992 | Marlin | 433/174 |
| 2002/0031749 A1 | | 3/2002 | Morgan | |
| 2004/0043360 A1 | * | 3/2004 | Obata | 433/173 |

FOREIGN PATENT DOCUMENTS

| | | |
|---|---|---|
| JP | 2005-052175 | 3/2005 |
| WO | WO 03/028580 A1 | 4/2003 |

* cited by examiner

*Primary Examiner* — Heidi M Eide
(74) *Attorney, Agent, or Firm* — Klauber & Jackson LLC

(57) ABSTRACT

A set of one-piece angled abutments, each abutment including an angled stump, a short intermediate cylindrical portion, and a lower threaded portion, wherein the placement of the starting point of the thread within the first round in the lower threaded portion of each abutment determines the angular orientation from 0° to 360° attained by the stump once the abutment is fully tightened to an implant located in the patient's mandible, the set has a variable number of abutments depending on the value of the constant angular offset chosen for spacing the beginning of the thread of each abutment included in the set, each set being defined by a constant angular offset with a value which is a divisor of 360 and the sets of abutments being accompanied by a circular box to easily select the abutment that attains the ideal angular orientation for a patient's needs.

2 Claims, 15 Drawing Sheets

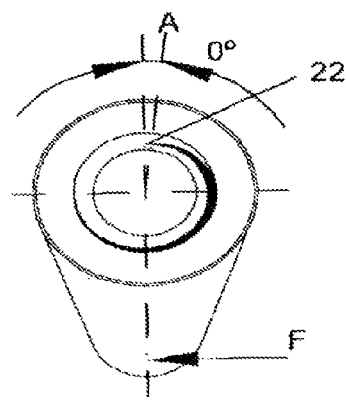
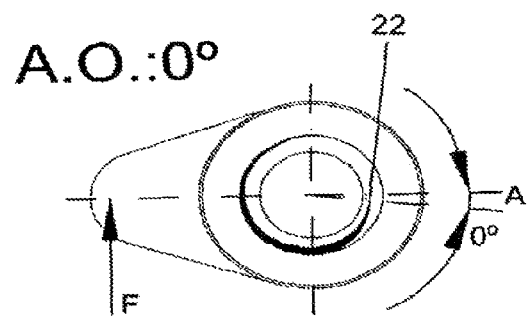
FIG. 6C
FIG. 6D
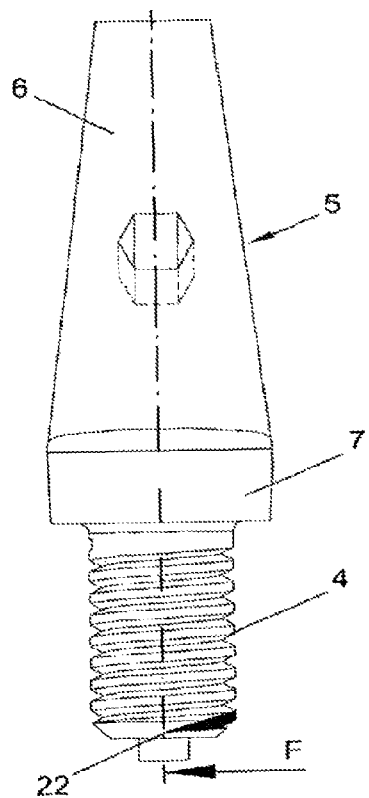
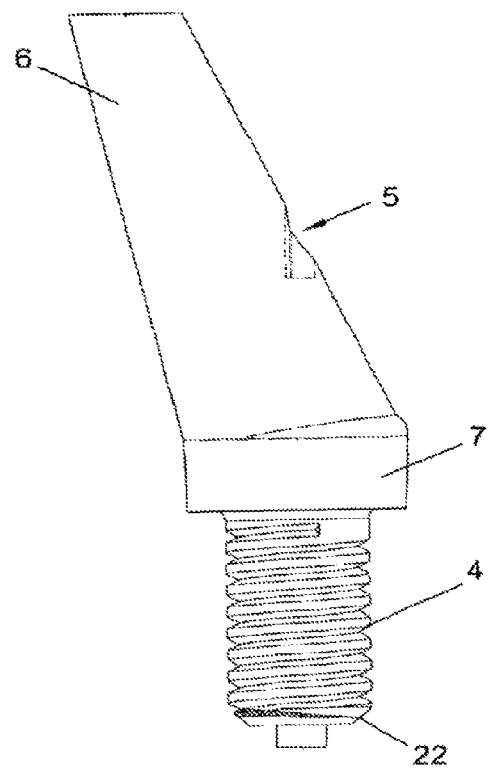
FIG. 6A
FIG. 6B

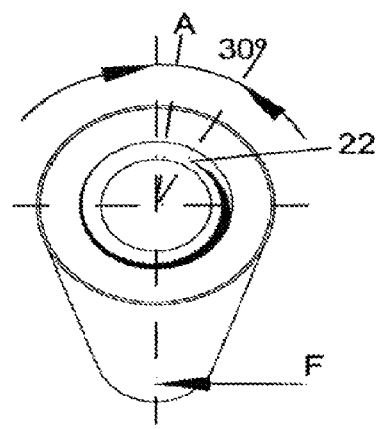
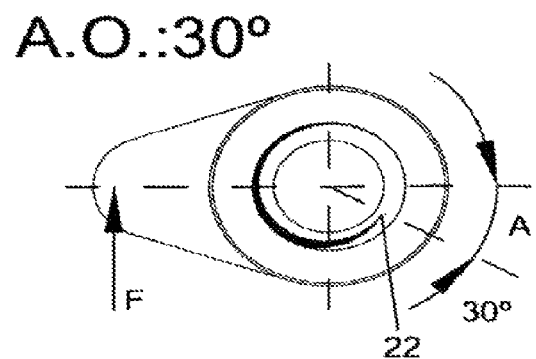
FIG. 7C
FIG. 7D
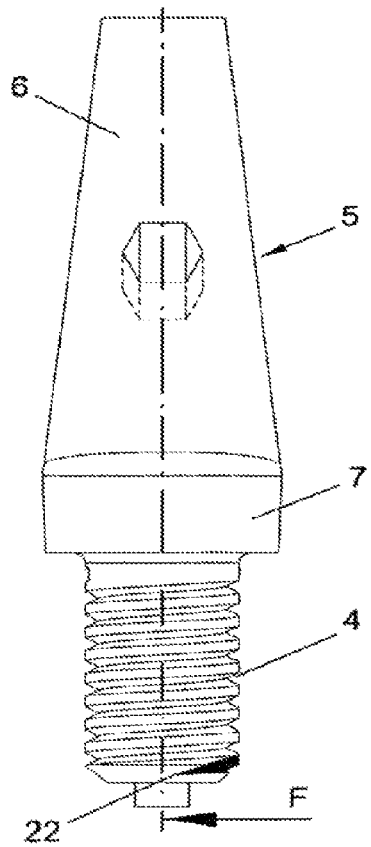
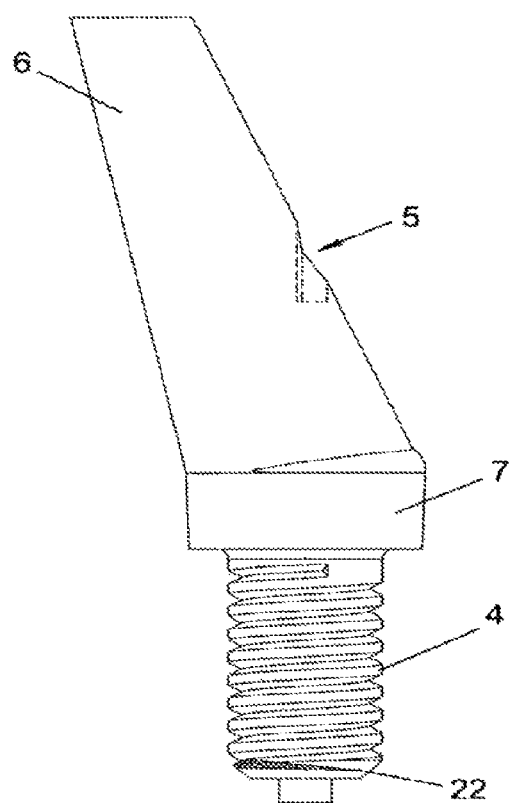
FIG. 7A
FIG. 7B

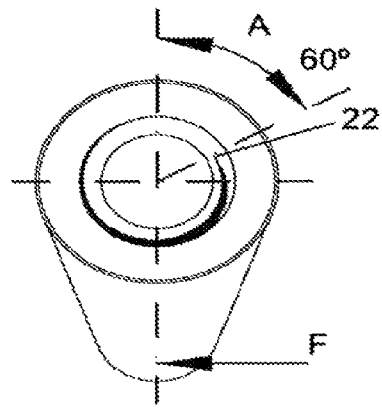
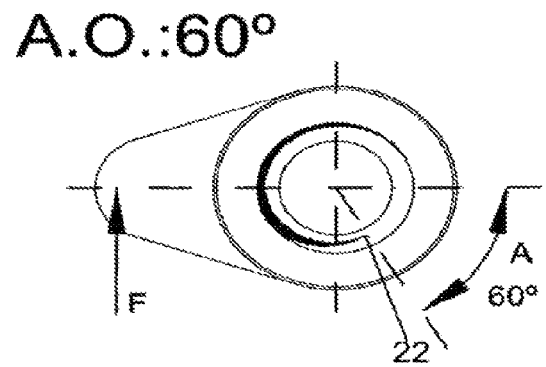
FIG. 8C    FIG. 8D
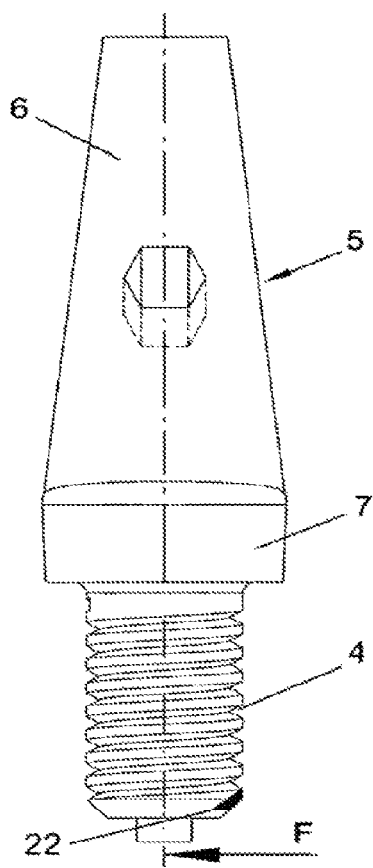
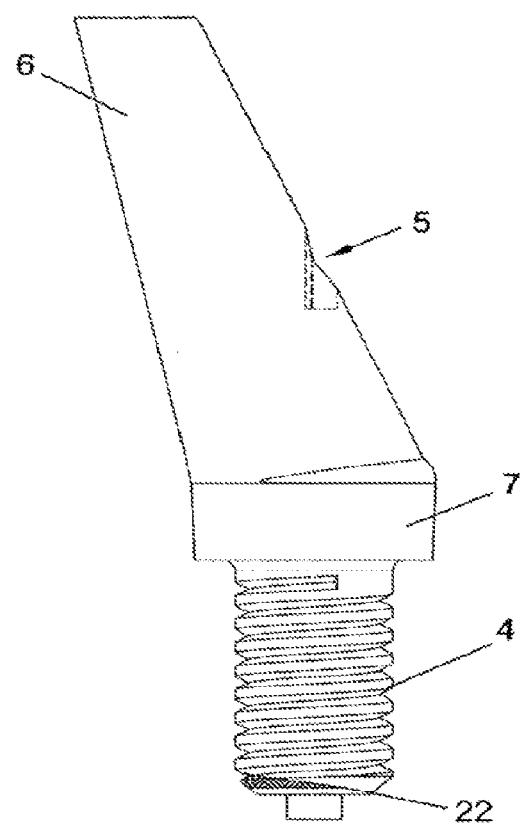
FIG. 8A    FIG. 8B

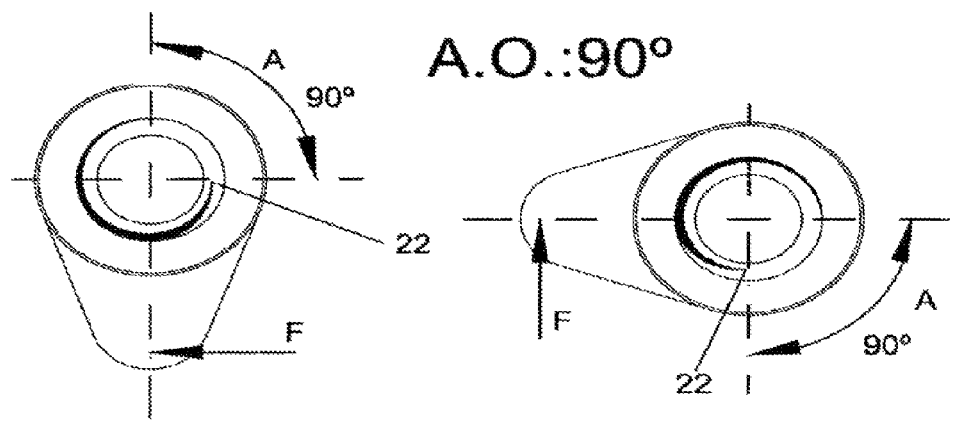
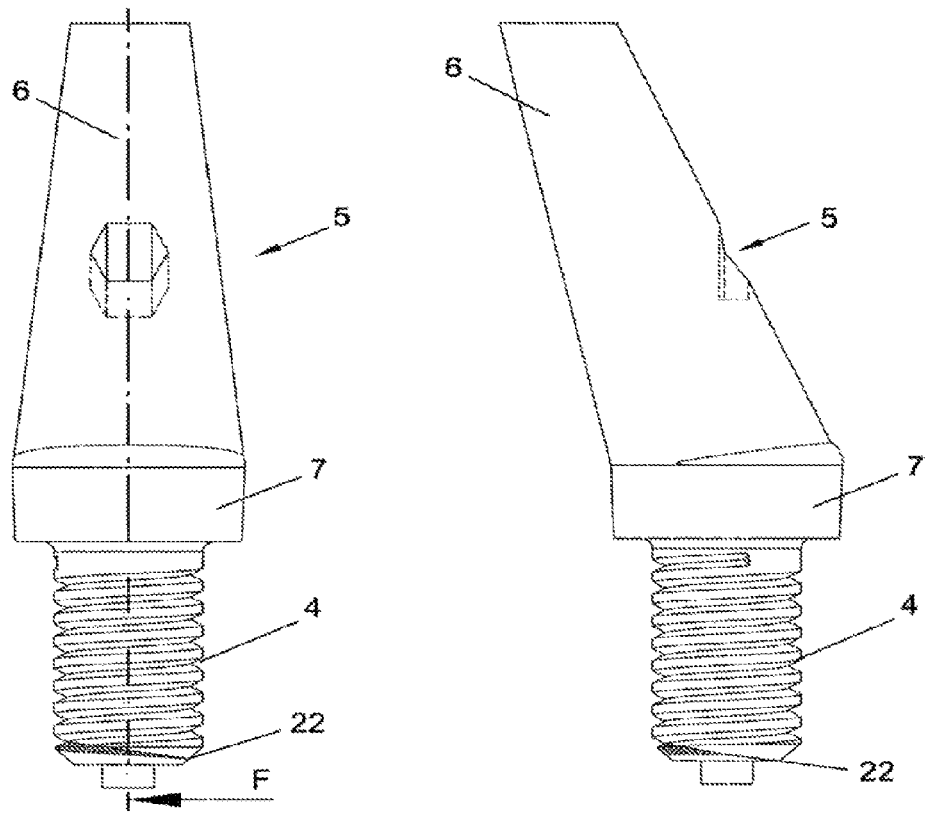

A.O.:120°

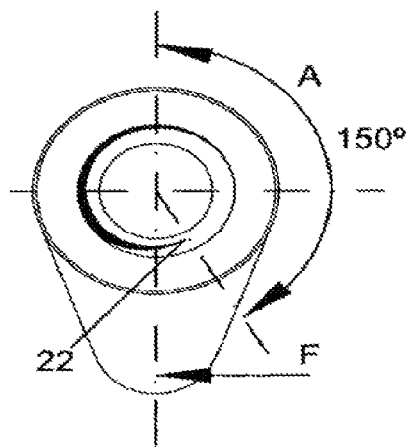
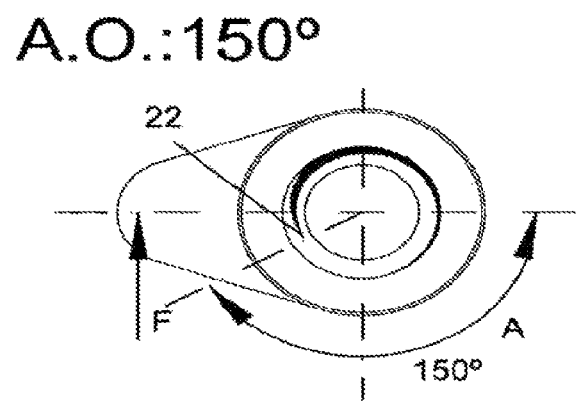
FIG. 11C    FIG. 11D
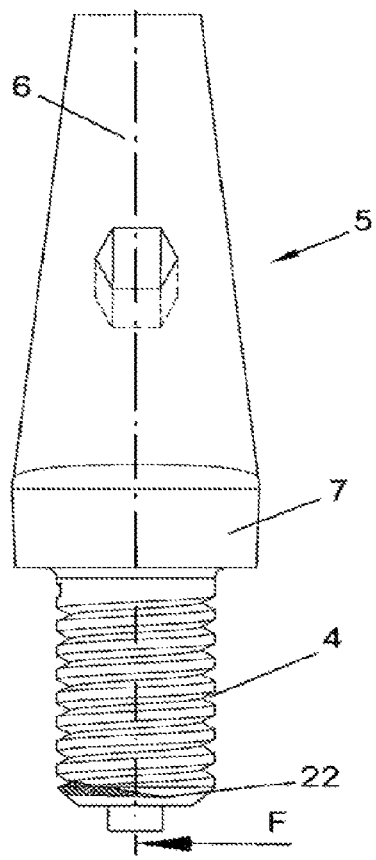
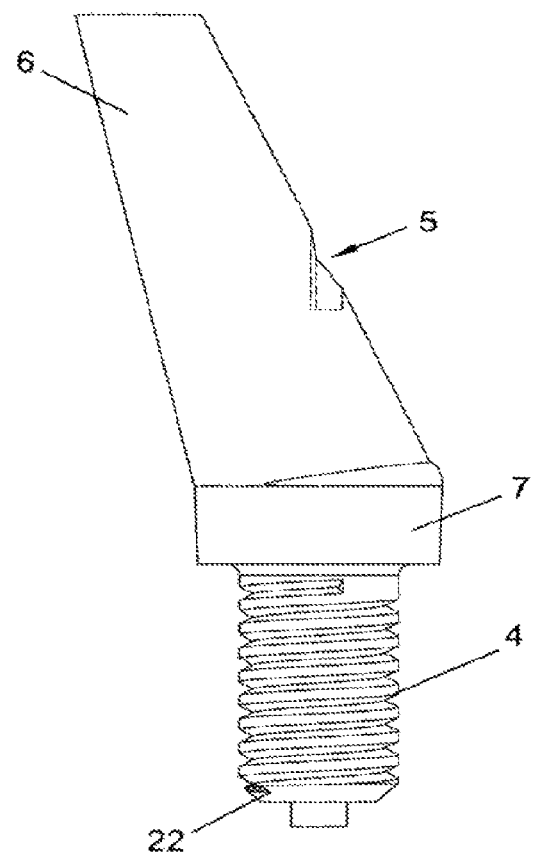
FIG. 11A    FIG. 11B

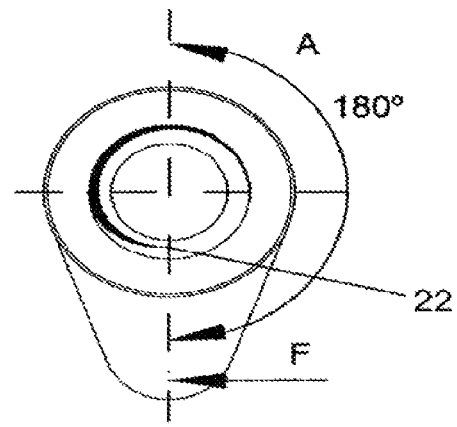
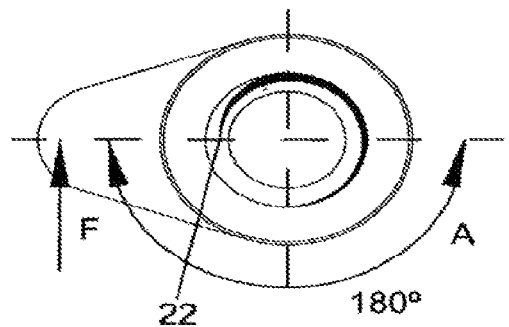
FIG. 12C  FIG. 12D
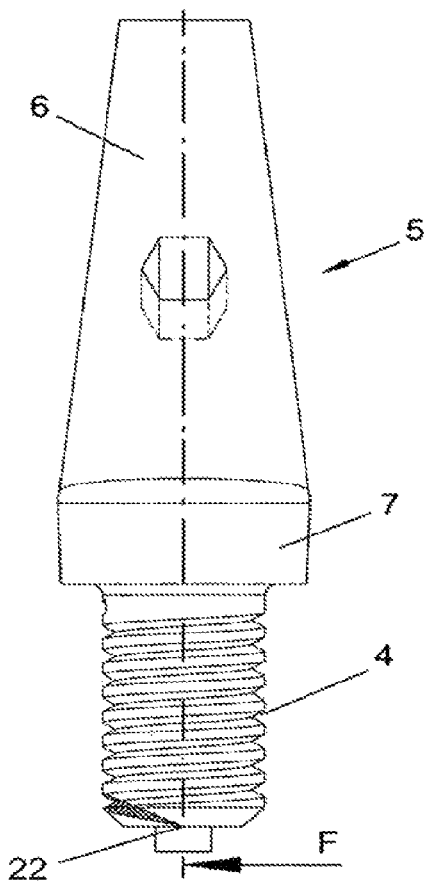
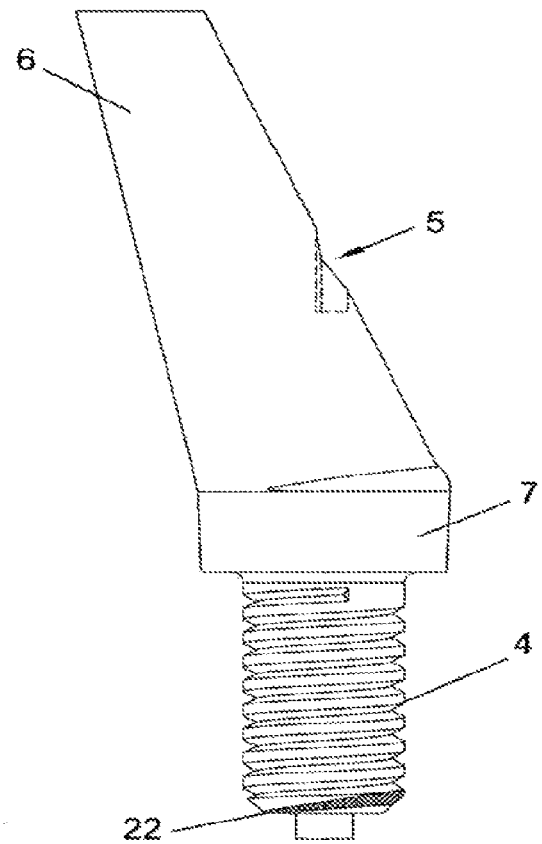
FIG. 12A  FIG. 12B

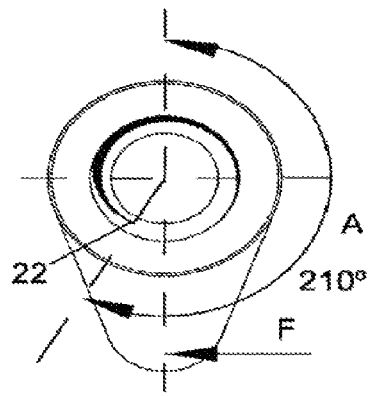
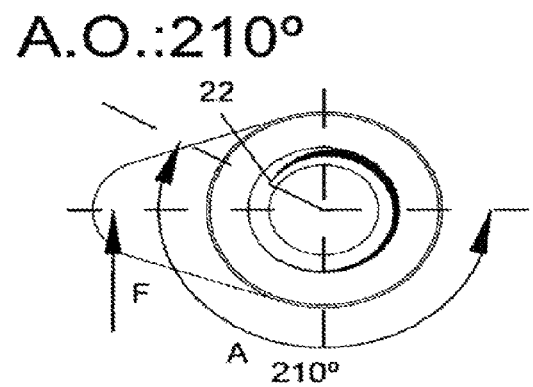
FIG. 13C
FIG. 13D
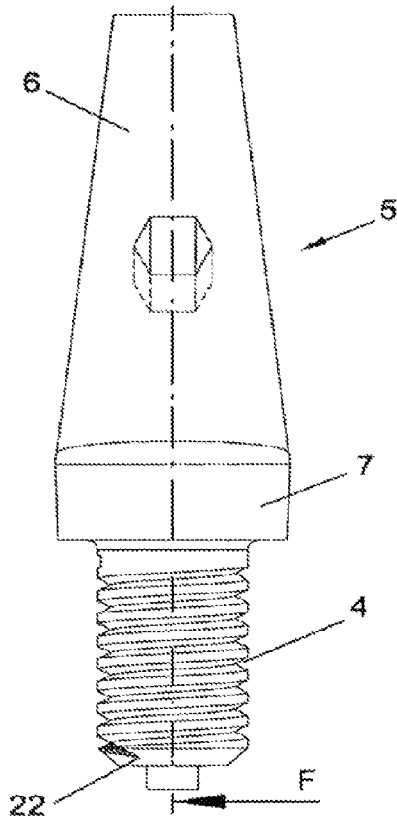
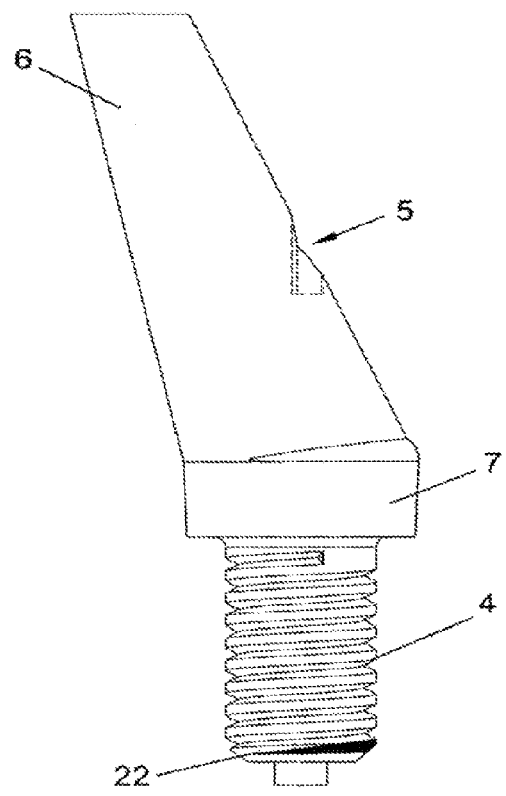
FIG. 13A
FIG. 13B

A.O.:240°

A.O.:270°

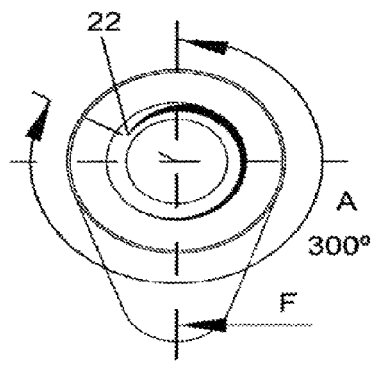
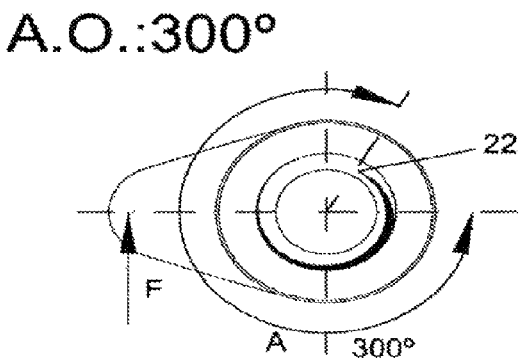
FIG. 16C  FIG. 16D
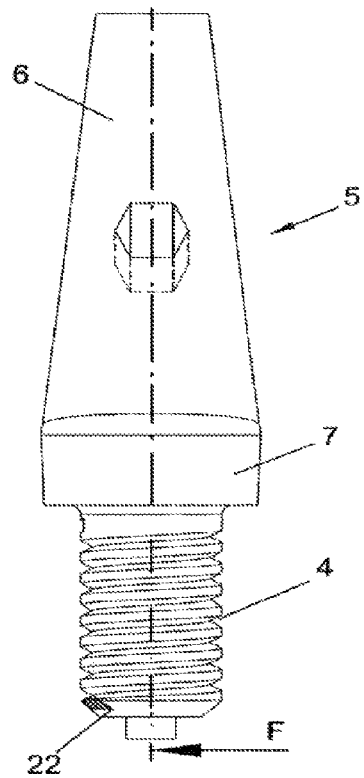
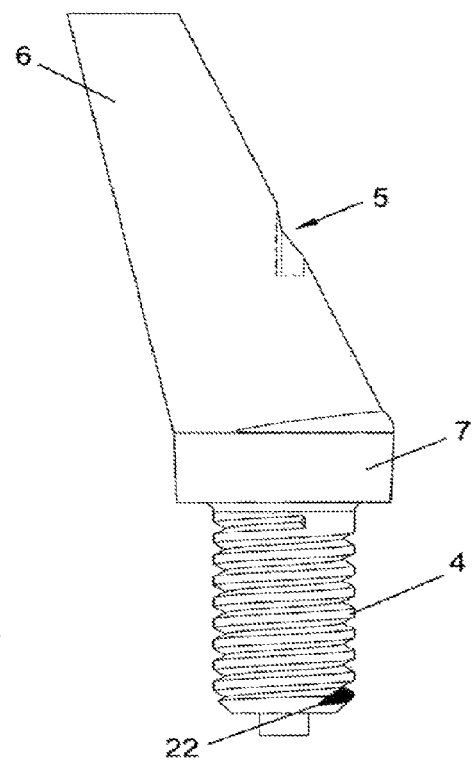
FIG. 16A  FIG. 16B

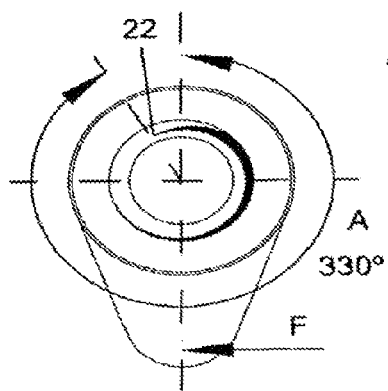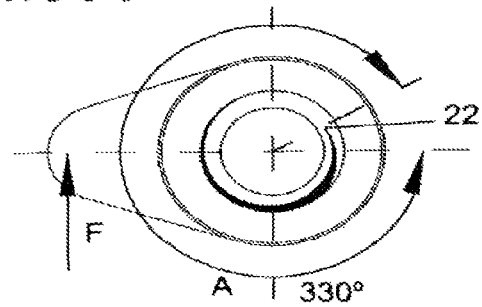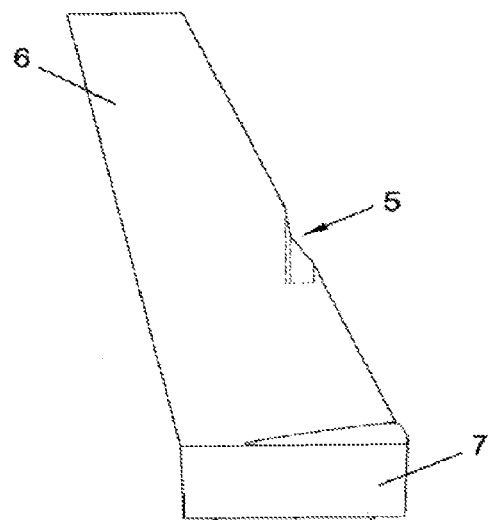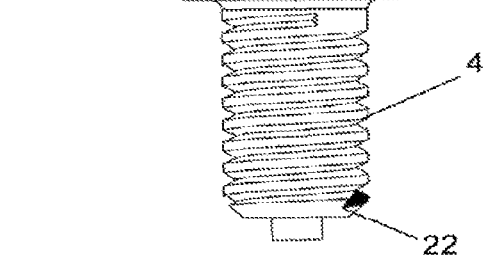
FIG. 17C  FIG. 17D
FIG. 17A  FIG. 17B

SET OF ONE-PIECE ANGLED ABUTMENTS

CROSS REFERENCE TO RELATED APPLICATIONS

The present patent application is a continuation-in-part of non-provisional U.S. patent application, Ser. No. 11/442,654, filed May 26, 2006 now abandoned which is, in turn, based upon and claims priority from Spanish Application Serial No. 200502461, filed Oct. 10, 2005. Applicants claim the benefits of 35 U.S.C. §120 as to the non-provisional application and priority under 35 U.S.C. §119 as to said Spanish application, and the entire disclosure of both applications are incorporated herein by reference in their entireties.

FIELD OF THE INVENTION

This invention refers, as expressed in the title of this specification, to an angled implant prosthesis configured in one piece and the method of use thereof.

Basically, the prosthesis comprises generally an implant attached to the bone of the patient's maxillary bones and an abutment's stump, or angled pillar, or prosthetic implant in turn attached to the implant, being the corresponding dental piece attached to said abutment.

Starting from this premise, the main objective of this invention is to obtain a one piece angled abutment and to avoid the loosening of the through screw of the traditional prosthetic implants over time.

Another objective of the invention is to provide the specific means to control the angular orientation or rotational position of the angled portion or stump of the one-piece angled abutment after being fully threaded to the implant attached to the patient's maxillary bones according to the needs of the dental piece in question.

A third objective of the invention is focused on the implant system, wherein a special tool or key participates to carry out the attachment of the angled abutment.

BACKGROUND OF THE INVENTION

Implant systems usually entail two types of pillars or prosthetic abutments' stumps to configure the fixed cemented prosthesis:

Straight abutments
Angled abutments

There are, generally, two types of straight abutments, those configured in one piece or those configured as a two-part piece. One piece abutments have the threaded portion and the emergent or prosthetic piece joined forming one piece.

In two piece abutments there is an hexagonal or an octagonal socket inside the implant, so that the hexagonal or octagonal platform placed in the lower portion of the abutment fits in the hexagonal socket of the implant and thus prevents the rotation of the emergent prosthetic piece. The whole piece is hollow and is internally traversed by a screw that affixes it to the implant (through screw), said screw being the second piece of the abutment.

Angled abutments are only manufactured in two pieces and follow the same principle as the two piece straight abutments.

There is a great diversity of hexagonal head screwdrivers which function is to screw the angled or straight portion to the implant.

On the other hand, an abutment in two pieces, whether straight or angled, will be screwed in a centric manner, which implies it is easy to use. However, with the passing of time and due to the action of grease, the through screw begins to loosen. Vibration caused by mastication forces and the fat contained in foodstuffs that filters through the joint between the implant and the false prosthetic abutment, or prosthetic pillar, or prosthetic implant, also influence the loosening of the through screw.

Another disadvantage of this system is that, although fitting the hexagon of the false prosthetic abutment to the implant outside the patient's mouth is easy, it becomes difficult when the implant is already set in place in the bone and under the gum, since soft tissue gets in the way and the slightest interposition of tissue results in an imperfect fit, obstructing the passage of the through screw, which creates subsequent problems such as the loosening and fracture of the titanium screw.

SUMMARY OF THE INVENTION

To attain the stated objectives and avoid the disadvantages mentioned in the above paragraphs, this invention proposes a one-piece angled abutment characterized in that it has its own means of attachment to an implant, placed in the maxillary bones of a patient, that can then receive the appropriate dental piece.

Thus, the present invention refers to a one-piece angled abutment to be used by threading means in an implant located in a patient's maxillary bones, said one-piece angled abutment comprising an abutment stump for affixing a prosthetic dental piece to said abutment stump and a lower threaded portion, wherein the threading means consist of a lower threaded portion integral with the abutment stump, the abutment stump has a truncated cone structure arising from a short intermediate cylindrical portion from whose base arises the lower threaded portion; the angled abutment stump with a truncated cone structure includes two generatrices forming different angles contained within the plane of symmetry of the one piece angled abutment: a larger or major angle, and a smaller or minor angle, and wherein said lower threaded portion has a starting point of the thread that is placed within an angular space ranging from 0° to 360°, which spans one round or pitch of the initial threaded portion at the bottom of the lower threaded portion, being 0° the position of the starting point of the thread coincident with the plane of symmetry of the abutment stump on the side of the larger angle.

The position of the starting point of the thread will achieve a specific angular orientation of the abutment stump after being tightened into the implant carried by the patient; and the angled abutment stump further comprises a cavity with a section different from the circular section.

The present invention entails a set of one-piece angled abutments comprising a number of one-piece angled abutments defined by an angular offset with a value which is a divisor of 360. The 0° position is the starting point of the thread in the lower threaded portion for the first angled abutment in the set of one-piece angled abutments. For each consecutive angled abutment comprised in the set, the starting point of the thread varies—or is displaced—along the 360° angular space in a value defining a rotating angular variation, being said value the "angular offset" or "angle portion variation". This means that the starting point of the thread at the bottom of said lower threaded portion in each abutment comprised in the set will vary in the 360° angular space according to a specific angular portion in such a way that the value in degrees of the angular portion will determine the number of abutments comprised in a set. This means that a rotating angular variation—or angular offset—of 60° will result in a set of six different angled abutments, an angular offset of 30° will result in a set of twelve different angled abutments, and so on.

This variation of the starting point of the thread from 0° to 360° that occurs in each angled abutment comprised in the set spans one round or pitch of the threading and results in a minute downward displacement of the threading along the lower threaded portion, while the length of the thread in said lower threaded portion remains constant, so that within a set of angled abutments, as the starting point of the thread is displaced from 0° to 360°, the distance from the beginning of the thread to the short intermediate cylindrical portion increases in very minute values.

The invention has also as an object a plurality of sets of one piece angled abutments as defined above, wherein each set is characterized by a different angular offset, measured in degrees, and each set of abutments is complemented by a circular box with as many independent compartments as there are abutments in a given set. The box contains the abutments ordered according to the position of the starting point of the thread within the 360° angular space and the angular orientation achieved by each angled abutment stump, and is further provided with a rotating lid in which there is a through hole to extract the selected abutment. This box in addition has a central coupling base consisting of a threaded socket similar to the threaded socket of the implant carried by the patient.

A characteristic of the invention is the specific means to orient the abutment in the desired radial plane, or angular orientation according to the placement of the implant in the maxillary bones inside the patient's mouth.

Said radial plane coincides with the definitive position of the prosthetic abutment in such a manner that the abutment has a lower threaded portion can be coupled with the threaded socket of the implant. Therefore, both the angular orientation of the upper part of the prosthetic abutment and the threaded lower portion will be contained in said radial plane. The abutment's stump includes a short base perpendicular to the threaded portion, from which said threaded portion arises.

The method of use is characterized in that it incorporates a special key that adapts to the inclination of the abutment counteracting said inclination, and above its base, in such a manner that the key is arranged in the same direction of the lower threaded portion or in a parallel direction close to the direction of said lower threaded portion.

In order to achieve this, the key is characterized in that it has a tubular section provided with a lateral window, through which part of the angled abutment peeks out. The upper part of the key above the lateral window presents a structure that allows manual handling or handling with a tool, to make the tightening and turning maneuver easier during the threading step of the abutment that affixes it to the implant.

The method of use is characterized in that the orientation of the prosthetic abutment depends on the structure of the lower threaded portion of said prosthetic abutment.

The method is based on a set of prosthetic abutments in which the starting point of the thread for each of them varies in a desired small angular portion, which serves to achieve the desired orientation of the prosthetic abutment's stump or pillar.

This variation covers the initial stretch of the thread corresponding to one round of the initial thread section of the lower abutment portion. The variation of the starting point of the thread results in a minute displacement of the thread along the lower threaded portion.

The method of use of the invention is complemented with a circular box with a central threaded socket similar to the threaded socket of the implant. The central threaded socket of the box serves as trial sample to try out and ensure the correct orientation of the abutment before it is coupled to the definitive implant inserted in the patient's maxillary bones.

Therefore an additional object of the invention is a method of use of the set of one-piece angled abutments comprising:
  providing means to orient the angled abutment in the desired radial plane or angular orientation according to an implant located in the patient's maxillary bone, the orientation of the stump of each one-piece angled abutment included in the set depending on the structure of the lower threaded portion,
  the starting point of the thread in the lower threaded portion of each angled abutment comprised in the set enables the attainment of a different angular orientation of the abutment stump once the abutment is fully threaded into the implant carried by the patient, allowing the selection of the most appropriate one
  providing a box, as defined above, with individual compartments containing a group of abutments ordered according to the position of the starting point of the thread within the 360° angular space and the angular orientation achieved by each angled abutment stump, the box having a central threaded socket, to be used as a reference and control check, that serves to try out and ensure the correct angular orientation of the one-piece angled abutment before it is threaded to the definitive implant carried by the patient,
  trying one-piece angled abutments contained in the box to find the one that fits the patient's needs.

The drawings below will serve to better understand the invention and method of use thereof. These drawings, that are an integral part of the present document, are to be understood as illustrative but not limiting of the scope of the invention.

BRIEF DESCRIPTION OF THE DRAWINGS

FIGS. 6A-17A show a back view illustrating a set of 12 abutments with an angular offset of 30°, said set including 12 angular orientations (A.O.): 0°, 30°, 60°, 90°, 120° 150° 180° 210°, 240°, 270°, 300°, and 330° respectively, and wherein 22 shows the beginning of the thread.

FIGS. 6B-17B show a left side view, rotated 90° with respect to the corresponding FIGS. 6A-17A, illustrating the same set of 12 abutments with an angular offset of 30° shown in FIGS. 6A-17A; wherein 22 shows the beginning of the thread.

FIGS. 6C-17C show a bottom back view of the abutments corresponding to FIGS. 6A-17A, illustrating the same set of 12 abutments with an angular offset of 30° shown in FIGS. 6A-17A; wherein 22 shows the beginning of the thread.

FIGS. 6D-17D show a bottom left side view, rotated 90° with respect to the corresponding FIGS. 6A-17A, illustrating the same set of 12 abutments with an angular offset of 30° of FIGS. 6A-17A; wherein 22 shows the beginning of the thread.

Figure 1:
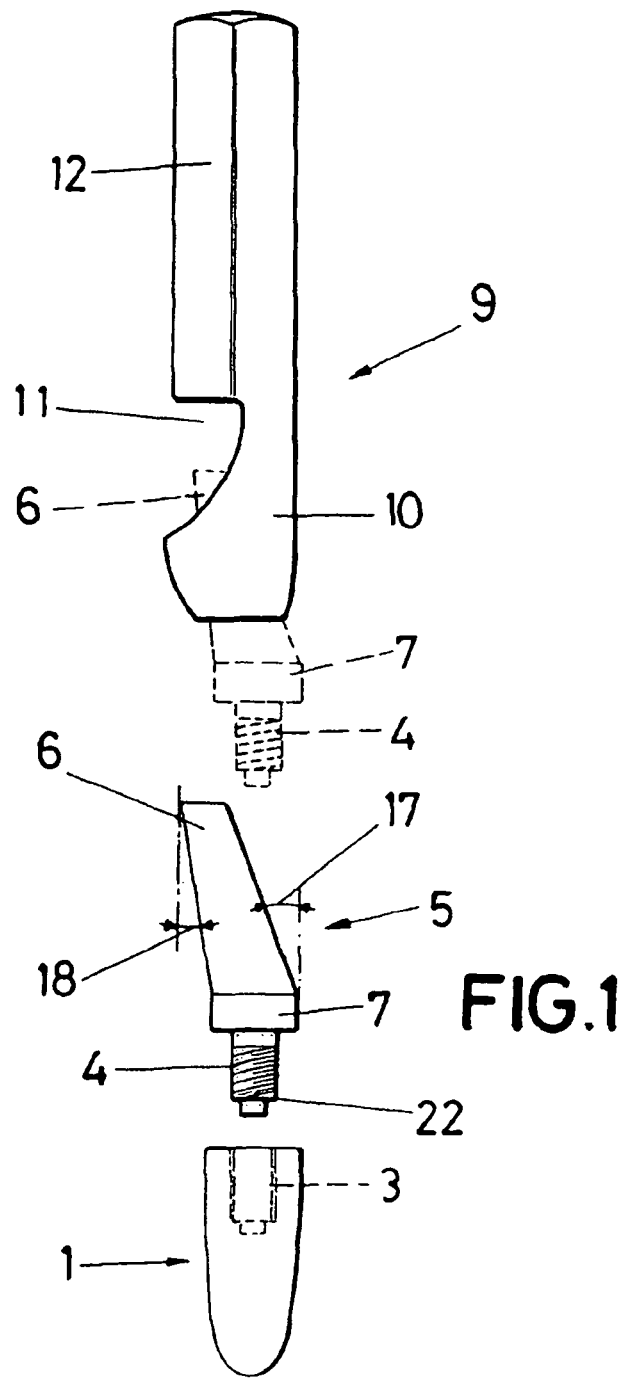
FIG. 1 Shows an exploded view of an angled prosthetic implant and method of use thereof, which is the objective of this invention.
Figure 2:
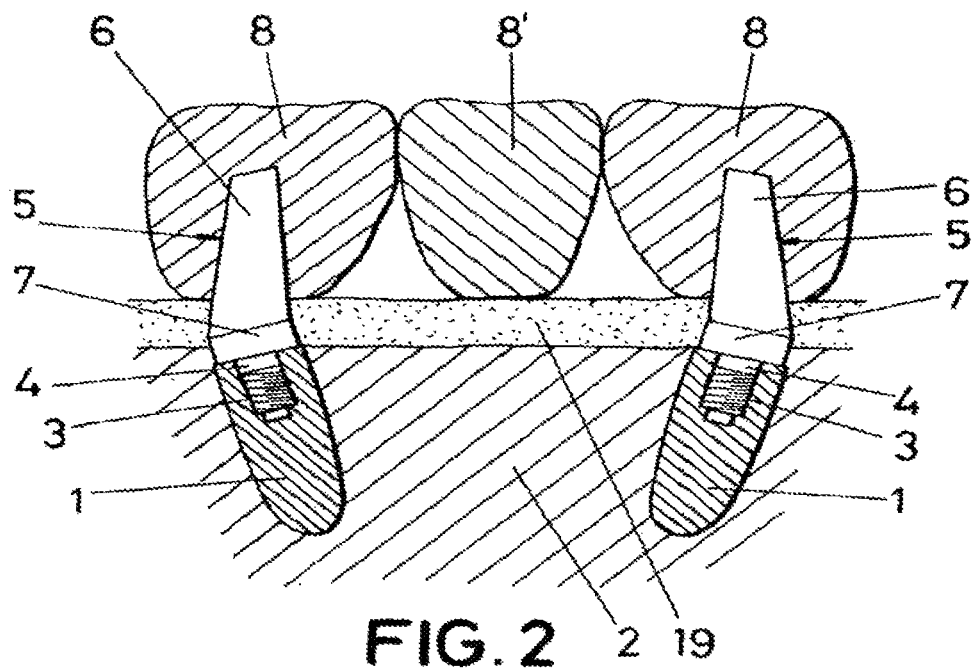
FIG. 2 Shows a view of the application of the prosthesis object of the invention.
Figure 3:
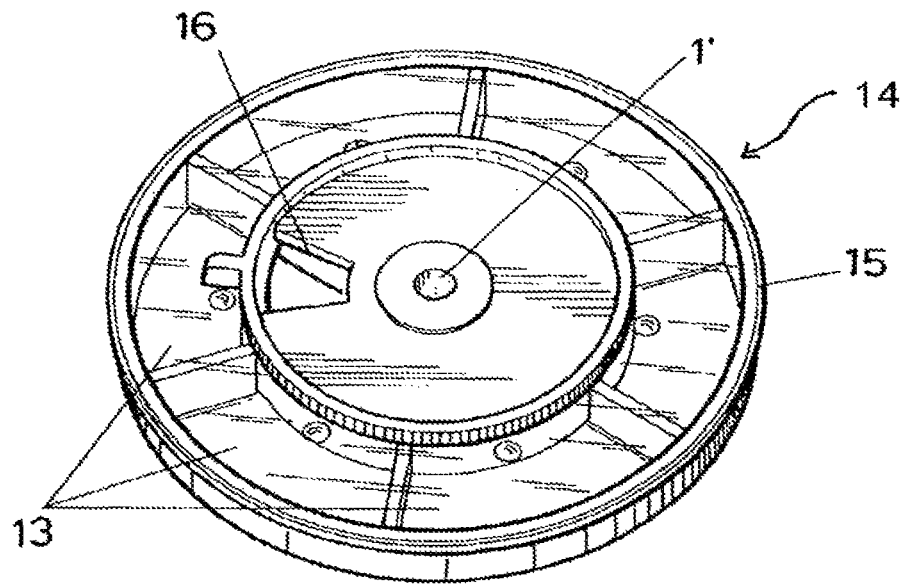
FIG. 3 Shows a view of a compartmentalized box housing a set of angled abutments. This box is part of the invention.
Figure 4:
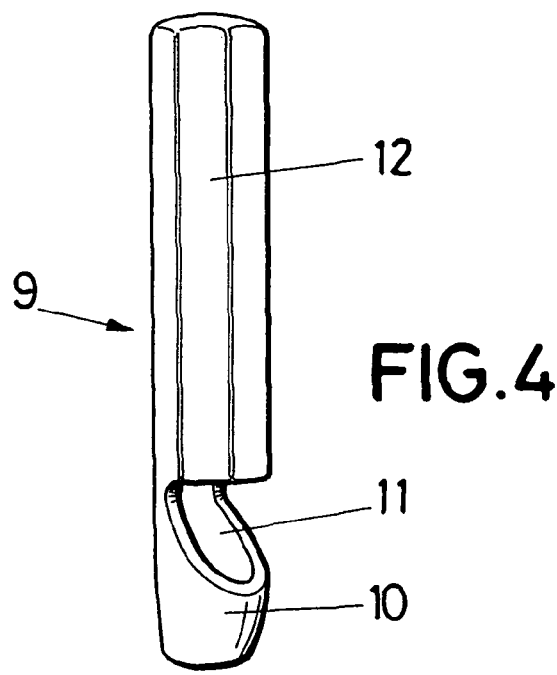
FIG. 4 Shows a perspective view of a special key that is also part of the invention.
Figure 5:
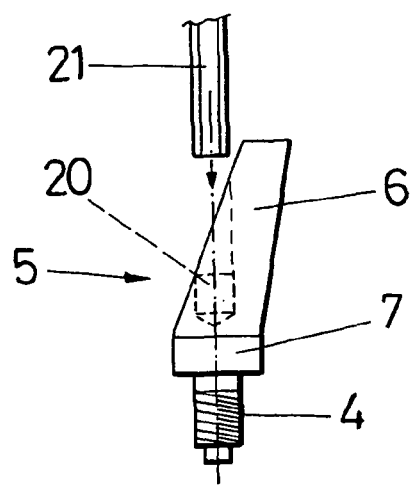
FIG. 5 Shows a view of a prosthetic implant tightened with a traditional key.

In some of the back and left side views the beginning of the thread is not visible and it is shown as a shaded area.

Angle A shows the radial displacement of the beginning of the thread, which coincides with the angular orientation.

F is a plane of symmetry that cuts the abutment in two symmetrical parts.

DESCRIPTION OF THE PREFERRED EMBODIMENT

Using the same number codes as those that appear in the Figures, the angled prosthetic implant is defined by an implant (1) affixed to the mandible (2) of a patient's bone, where said implant (1) has a threaded socket (3) to which is coupled a lower threaded section (4) that is part of a mono-piece angled abutment 5 with an angled abutment stump (6) having a truncated cone structure that rises out of a short intermediate cylindrical section (7) and from whose free base starts said threaded portion (4).

The required dental piece (8) will be affixed over said prosthetic abutment's stump (6).

In a preferred embodiment the one-piece angled abutment 6 is to be used by threading means in an implant (1) located in a patient's mandible, said one-piece angled abutment 6 comprising an abutment stump (5) for affixing a prosthetic dental piece to said abutment stump and a lower threaded portion, wherein the threading means consist of a lower threaded portion (4) integral with the abutment stump (5), the abutment stump has a truncated cone structure arising from a short intermediate cylindrical portion (7) from whose base arises the lower threaded portion 4; the angled abutment stump (6) with a truncated cone structure includes two generatrices forming different angles contained within the plane of symmetry (F) of the one piece angled abutment: a larger or major angle (17), and a smaller or minor angle (18), and wherein said threaded portion (4) has a starting point of the thread (22) that is placed within an angular space ranging from 0° to 360°, which spans one round of the initial threaded portion (4), being 0° the position of the starting point of the thread (22) coincident with the plane of symmetry of the abutment stump on the side of the larger angle (18).

The position of the starting point of the thread (22) will achieve a specific angular orientation of the abutment stump (6) after being tightened into the implant (1) carried by the patient; and the angled abutment stump (5) further comprises a cavity (20) with a section different from the circular section.

Coupling and affixing of the abutment (5) is done, first, by a special key (9) that has, at least, one tubular lower portion (10) provided with a lateral window (11) and an upper portion (12) with an hexagonal cross-section, or with any other geometrical configuration, to handle said key (9) so it can be turned to thread the angled abutment (5) onto the appropriate implant (1).

To do this, the tilted abutment's stump (6) is inserted first in the inner space of the lower tubular portion (10) of key (9) until it peeks out of the lateral window (11), at which point, key (9) will be placed pointing in the same direction than the lower threaded portion (4) and acting as a continuation of said portion. Once in this position, the procedure can continue by coupling and affixing the angled abutment (5), threading it by turning the key (9), which motion will obviously drag with it the abutment (5).

To obtain the desired angular orientation of the abutment (5) in relation to the axis of rotation of its threaded portion the starting point of the threading (22) of this portion will vary in a 360 [deg.] angular space in as many partial angle portions as desired by the manufacturer or the designer.

The variation of the beginning of the thread to obtain the desired orientation further produces a minute displacement of the threaded section along the lower threaded portion (4).

The prosthesis featured by this invention presents, amongst others, one first advantage by having a structure of greater solidity achieved by the angled abutment being in one piece, and a second advantage that resides in that the abutment is affixed by threading it with a rotational motion, and therefore it will never be badly installed, even when soft gum tissue (19) gets in the way, since the threading motion serves to remove the tissue from the gum as it progresses.

The special key (9) threads the angled abutment (5) in a centrally oriented manner when the abutment is already set in place inside the tubular portion (10) of key (9) and peeking out lateral window (11).

This fitting of the abutment and the key absorbs the angulation retaining it in place inside the key and avoiding the falling of the abutment during the time prior to actual installation, which is the most delicate stage of the procedure, since the piece could fall inside the patient's mouth cavity causing the expected problems.

Once the prosthesis set is assembled its immobilization is ensured by the mono-piece abutment structure that includes the tilted abutment stump (6) and the threaded portion (4), in such a manner that the dental piece will abut tangentially against an adjacent dental piece (8') to prevent its unthreading.

The tilted abutment stump presents a truncated conical cross section that when considering the plane of the direction of the abutment stump, a first major angle (17) is created between a generatrix of the stump and a perpendicular line, that is parallel to the threaded portion, said line and said generatrix being contained within the plane. This is the only symmetry plane of the one-piece angled abutment (5) and of the abutment stump (6), and is shown as F in the figures.

A second minor angle (18) is also generated between a second generatrix contained in said symmetry plane F and another perpendicular line as the one mentioned in the previous paragraph.

Figure 10C:
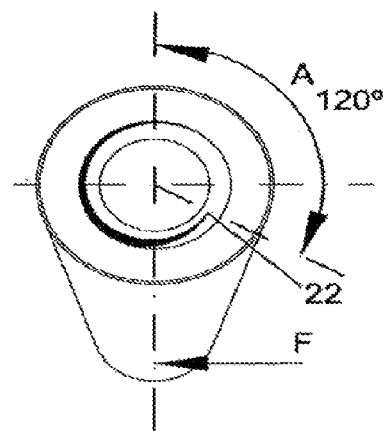
Figure 10D:
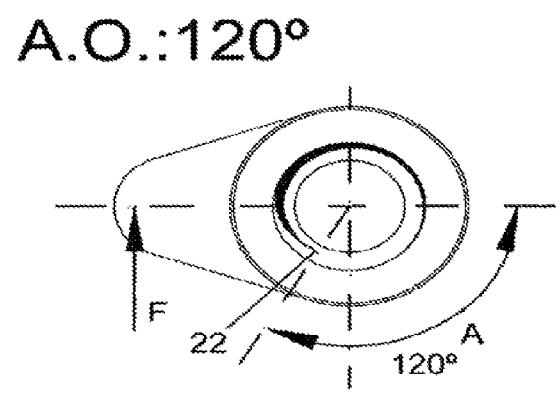
Figure 10A:
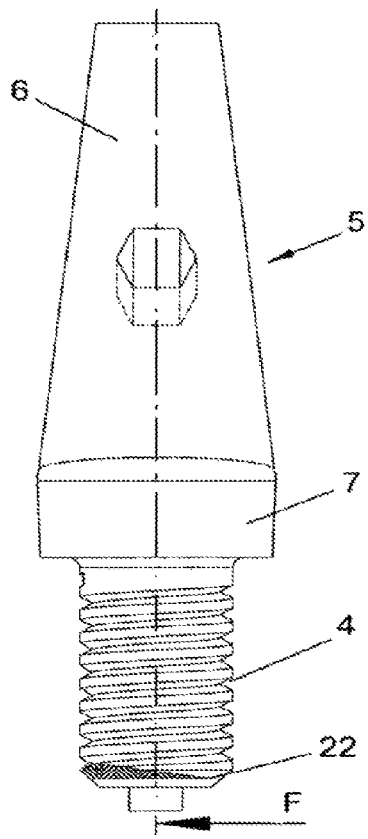
Figure 10B:
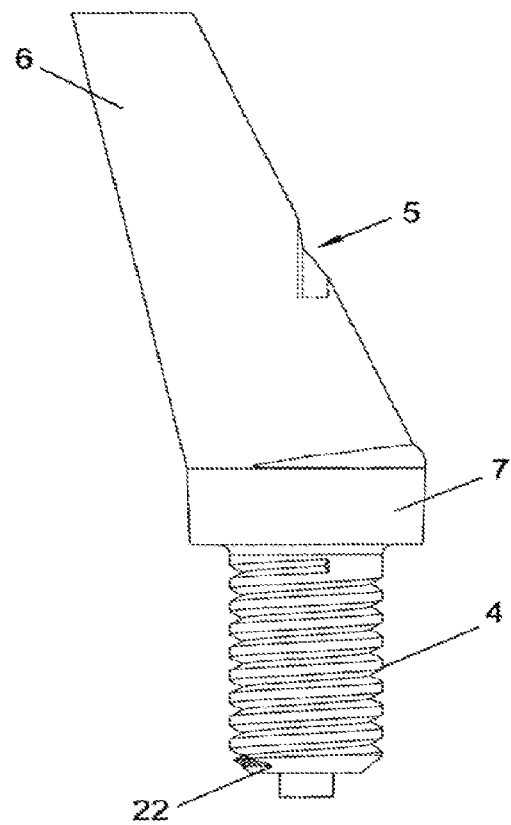
Figure 14C:
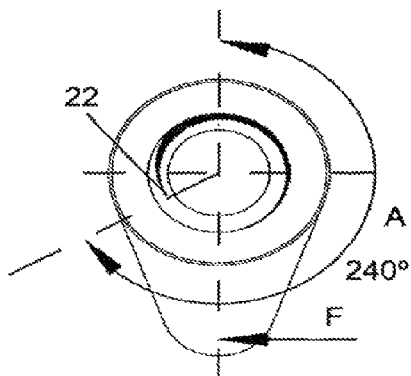
Figure 14D:
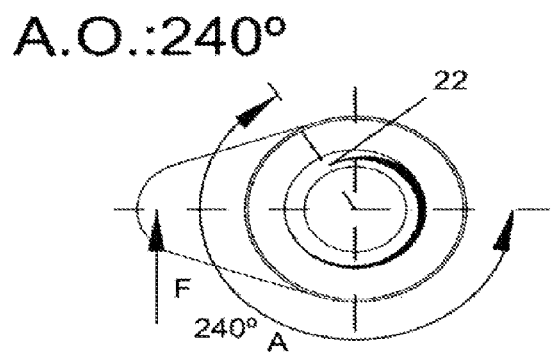
Figure 14A:
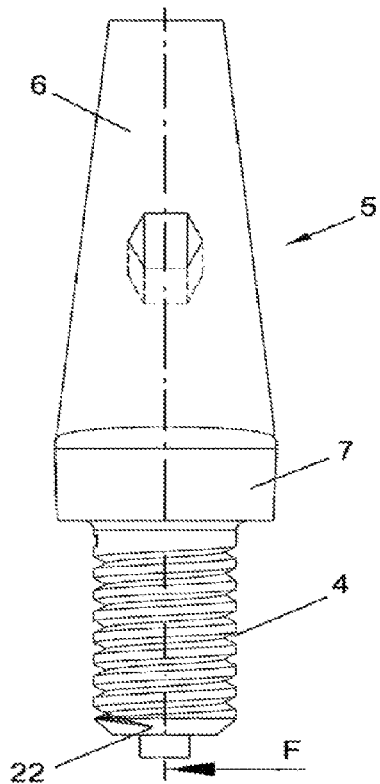
Figure 14B:
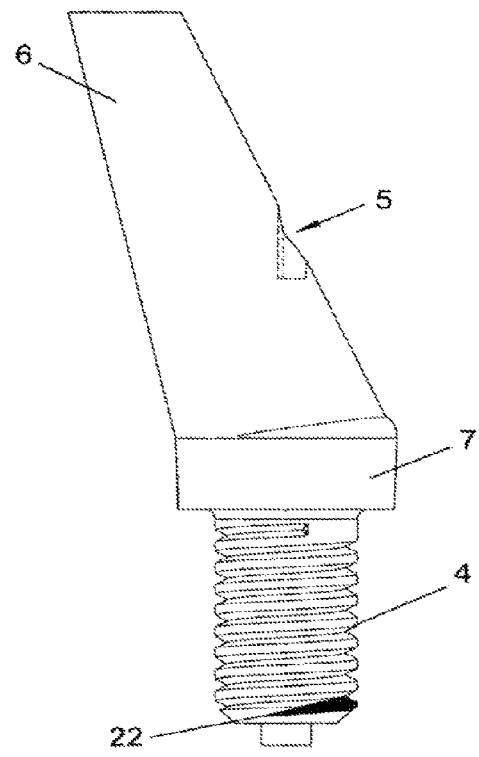
Figure 15C:
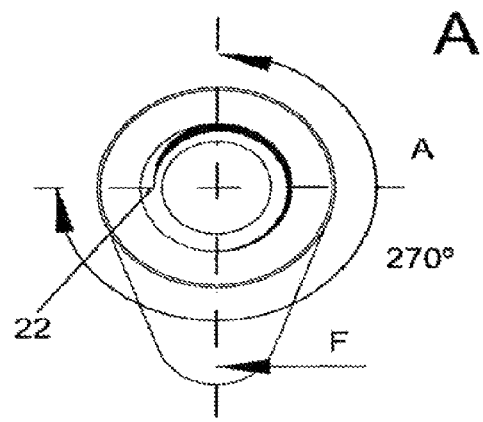
Figure 15D:
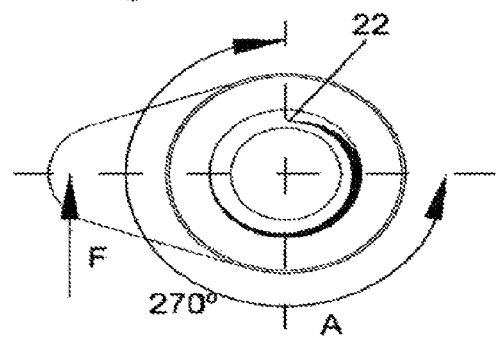
Figure 15A:
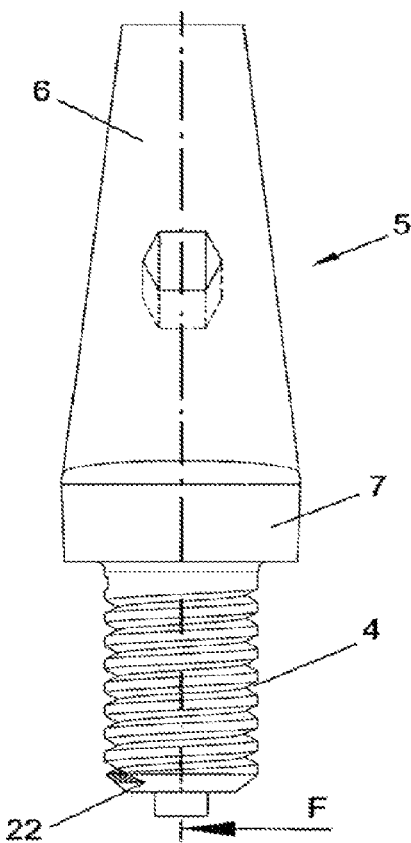
Figure 15B:
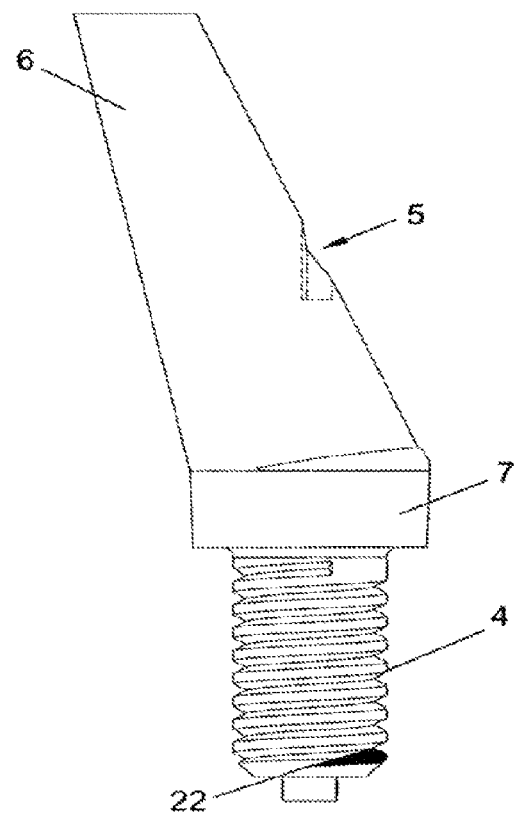

In order to encompass any desired angle position of the abutments, the invention includes sets of like abutments wherein the final rotating angular variation after being tightened is, for instance, 12[deg.], 15[deg.], 30[deg.], 60[deg.], or any other value. According to the preceding paragraph, FIGS. 6A-17A show a back view illustrating a set of 12 abutments with an angular offset of 30°, said set including 12 angular orientations (A.O.) 0°, 30°, 60°, 90°, 120°, 150°, 180°, 210°, 240°, 270°, 300°, and 330° respectively, and wherein 22 shows the beginning of the thread, FIGS. 6B-17B show a left side view, rotated 90° with respect to the corresponding FIGS. 6A-17A, illustrating the same set of 12 abutments with an angular offset of 30° shown in FIGS. 6A-17A, wherein 22 shows the beginning of the thread, FIGS. 6C-17C show a bottom back view of the abutments corresponding to FIGS. 6A-17A illustrating the same set of 12 abutments with an angular offset of 30° shown in FIGS. 6A-17A; wherein 22 shows the beginning of the thread and FIGS. 6C-17D show a bottom left side view, rotated 90° with respect to the corresponding FIGS. 6A-17A, illustrating the same set of 12 abutments with an angular offset of 30° of FIGS. 6A-17A; wherein 22 shows the beginning of the thread.

This set of abutments will be located in independent compartments (13) of a box (14) provided with a transparent and rotating lid (15) with a through hole (16) that allows the selection and extraction of the desired abutment.

To this effect every compartment will contain a group of prosthetic abutments of a specific angular variation.

Also, in the centre of box (14) there is a threaded socket(1') similar to the threaded socket (3) of the implant (1) to be used as reference and control check for the selected prosthetic abutment.

The prosthetic abutment's stump (6) can incorporate a cavity (20) with any given section different from the circular section that will fit the appropriate tightening key (21).

The invention has been described in an illustrative manner, and it is to be understood that the terminology, which has been used is intended to be in the nature of words of description rather than of limitation.

While the present invention has been set forth in terms of a specific embodiment or embodiments, it will be understood that the equipment herein disclosed may be modified or altered by those skilled in the art to other configurations, and that the invention includes variations in form, size, parts and details of operation within its scope. Accordingly, the invention is to be broadly construed and limited only by the scope and spirit of the claims appended hereto.

All publications, including but not limited to patents and patent applications, cited in this specification are herein incorporated by reference as if each individual publication were specifically and individually indicated to be incorporated by reference herein as though fully set forth.

LIST OF REFERENCES USED IN THE DRAWINGS 1 implant
1' threaded socket of the central coupling base of the box
2. maxillary bones
3 threaded socket
4 lower threaded portio
5 one-piece angled abutment (5)
6 abutment stump
7 intermediate cylindrical portion (7)
8, 8' dental piece
9 key
10 tubular portion 10 of key
11 lateral window
12 upper portion of the key
13 independent compartments of the box
14 box
15 rotating lid
16 through hole of the lid
17 larger angle
18 minor angle
19 gum tissue
20 cavity
21 tightening key
22 starting point of the thread
F plane of symmetry
A.O. angular orientation

The invention claimed is:

1. A kit including a plurality of sets of one-piece, angled abutments, to be used by threading means in a conventional implant located in a patient's mandible, each one-piece angled abutment included in the set comprising an angled abutment stump which includes a truncated cone structure, a non-cylindrical cavity, a short intermediate cylindrical section, and a lower threaded portion, which comprises a starting point of the thread placed within a 360° angular space spanning one round of thread in the lower threaded portion; for each one-piece angled abutment of the set, a position of the starting point of the thread of the lower threaded portion varies in a desired angular portion within the 360° angular space spanning one round of thread in the lower threaded portion, producing an angular variation of the position of the starting point of the thread of the lower threaded portion to achieve a desired angular orientation of the angled abutment stump in relation to an axis of rotation of the lower threaded portion after the one-piece angled abutment is fully threaded in said conventional implant located in a patient's mandible, and the kit further comprising a plurality of circular boxes for use with said sets, wherein;

each set is characterized by a different angular portion, measured in degrees, for the angular variation of the starting point of the thread, and each set is complemented by one of the circular boxes with as many independent compartments as there are one-piece angled abutments in each set, the individual compartments containing the one-piece angled abutments ordered according to the position of the starting point of the thread within the 360° angular space and the angular orientation achieved by each angled abutment stump, and the circular box is further provided with a rotating lid in which there is a through hole to extract the one-piece angled abutments, the circular box in addition has a central coupling base consisting of a central threaded socket where the one-piece angled abutments comprised in the set can be threaded in order to visualize the angular orientation achieved by the one-piece angular abutments.

2. A method of use of a kit, as described in claim 1, the method comprising:

organizing the one-piece angled abutments of the set according to the position of the starting point of the thread and the resulting angular orientation achieved by the angled abutment stump, in the independent compartments of the circular box provided with the rotating lid with the through hole allowing the selection and extraction of a desired one-piece angled abutment, trying out the desired one-piece angled abutment in the central threaded socket of the circular box to ensure the correct angular orientation of the desired one-piece angled abutment before said desired one-piece angled abutment is threaded to the conventional implant carried by the patient, and screwing the selected desired one-piece angled abutment in the conventional implant located in the patient's mandible.

* * * * *